US00PP12774P2

(12) United States Plant Patent
Zaiger et al.

(10) Patent No.: US PP12,774 P2
(45) Date of Patent: Jul. 16, 2002

(54) INTERSPECIFIC TREE NAMED 'TASTY RICH'

(76) Inventors: Chris Floyd Zaiger, 929 Grimes Ave.; Gary Neil Zaiger, 1907 Elm Ave.; Leith Marie Gardner, 1207 Grimes Ave.; Grant Gene Zaiger, 4005 California Ave., all of Modesto, CA (US) 95358

( * ) Notice: Subject to any disclaimer, the term of this patent is extended or adjusted under 35 U.S.C. 154(b) by 148 days.

(21) Appl. No.: 09/767,778

(22) Filed: Jan. 24, 2001

(51) Int. Cl.[7] ..... A01H 5/00
(52) U.S. Cl. ..... Plt./180
(58) Field of Search ..... Plt./180

*Primary Examiner*—Bruce R. Campell
*Assistant Examiner*—Anne Marie Grünberg

(57) ABSTRACT

A new and distinct variety of Interspecific Tree. The following features of the tree and its fruit are characterized with the tree budded on Nemaguard Rootstock (unpatented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consists of the following unique combination of features that are desirable in a new variety:

1. Heavy and regular production of fruit.
2. Fruit with excellent flavor and eating quality.
3. Fruit that has firmer flesh than standard apricots in California.
4. Produces medium to large size freestone fruit with an attractive yellow orange skin color.

1 Drawing Sheet

BACKGROUND OF THE VARIETY

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of interspecific tree was originated and asexually reproduced by us in an experimental orchard located near Modesto, Stanislaus County, Calif.

PRIOR VARIETIES

Among the existing varieties of plums, apricots and interspecifics which are known to us, and mentioned herein, Royal Zee Plum (U.S. Plant Pat. No. 5,486), Flaming Gold Apricot (U.S. Plant Pat. No. 2,822), Red Beaut Plum (U.S. Plant Pat. No. 2,539) and Honey Rich Interspecific (U.S. Plant Pat. No. 10,292).

ORIGIN OF THE VARIETY

The present new and distinct variety of interspecific tree [*Prunus armeniaca*×((*Prunus armeniaca*×(*Prunus salicina*×*Prunus armeniaca*)×*Prunus salicina*)], was originated by us in our experimental orchard located near Modesto, Calif., as a 1991 first generation cross between an apricot of unknown parentage and the interspecific seedling with field identification number 7HC43. The paternal parent (7HC43) originated from a cross between the selected seedling 87EB90 (apricot×plum cot) with Royal Zee Plum (U.S. Plant Pat. No. 5,486). The selection (87EB90) originated from an open pollinated Flaming Gold Apricot (U.S. Plant Pat. No. 2,822) seedling crossed with a plum cot seedling, which originated from an open pollinated Red Beaut Plum (U.S. Plant Pat. No. 2,539) seedling. We planted and maintained a large group of these first generation interspecific seedlings, growing on their own root system, under close observation, during which time one interspecific seedling, which is the present variety, exhibited very desirable fruit characteristics and was selected for asexual propagation and commercialization.

ASEXUAL REPRODUCTION OF THE VARIETY

Asexual reproduction of the new and distinct variety of interspecific tree was by budding to Nemaguard Rootstock, (unpatented) one of the standard rootstocks for interspecific trees in California, as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

Our present new and distinct variety of interspecific tree [Apricot×(Apricot×(Plum cot)×Plum)] is of large size, semi-spreading growth and a productive and regular bearer of medium to large, firm, yellow flesh, freestone fruit with excellent flavor and eating quality. The new variety grows similar to an apricot tree with a slightly rougher bark condition throughout the tree. The fruit is similar to apricot in appearance with the exception of being more round in shape than standard apricots and the skin and flesh color being a lighter yellow orange color. The flesh firmness and texture is firmer and meatier than standard apricots and the flavor is excellent, predominately apricot, but suggestive of plum with desirable lingering aftertaste. In comparison to the interspecific tree Honey Rich (U.S. Plant Pat. No. 10,292) the fruit of the new variety has a lighter, yellow orange skin color and is 14 days earlier in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of interspecific tree, its flowers, foliage and fruit, as based on observations of specimens grown near Modesto, Calif., with color terminology (except those in common terms) in accordance with Reinhold Color Atlas by A. Kornerup and J. H. Wanscher.

Tree:

*Size.*—Large. Tree pruned to 10 to 12 feet in height and width for economical harvesting of fruit.

*Vigor.*—Vigorous, growing 6 to 7 feet in height and 4 to 6 feet in width the first growing season, pruned in dormant season to select desired scaffolds.

*Growth.*—Semi-spreading. Crotch angle approximately 45°, weight of fruit tends to spread tree.

*Productivity.*—Productive. Usually sets adequate fruit, only light thinning and spacing of fruit is necessary.

*Bearer.*—Regular. Has had 6 consecutive years of adequate fruit set. No alternate bearing observed.

*Fertility.*—Self sterile, pollenizer required.

*Density.*—Medium dense. Pruned to vase shape to allow more sunlight to center of tree, enhances brix, color of fruit and improves growth of fruit bearing wood.

*Hardiness.*—Hardy in all stone fruit growing areas in California. Tree growing in USDA Zone 9. Chilling requirement approximately 700 hours.

Trunk:

*Size.*—Large, stocky. Average circumference of 16 inches measured 12 inches above ground on 6 year old tree.

*Surface.*—Medium shaggy.

*Texture.*—Rough. Roughness increases with age of tree.

*Color.*—Brown to dark brown (6-E-7) to (6-F-8). Color becomes darker with age of tree.

Branches:

*Size.*—Average circumference of 10½ inches measured at 36 inches above ground on 6 year old tree. Crotch angle approximately 45°.

*Surface.*—Varies from smooth on new growth to medium rough on old growth. Roughness increases with age of tree.

*Lenticels.*—Numerous — average number 49 in 4 square inch surface area. Small. Average length 3/32 inch. Average width 3/64 inch. Color varies from grayish orange to golden yellow (5-B-4) to (5-B-5).

*Color.*—First year growth — upper surface garnet brown (9-D-8), lower surface pastel green (30-A-4). Older growth varies from sepia brown to olive brown (4-F-5) to (4-F-6). Color becomes darker with age of branch.

Leaves:

*Size.*—Large. Average length 3 9/32 inches. Average width 2 29/32 inches.

*Form.*—Ovate.

*Margin.*—Serrate.

*Thickness.*—Medium.

*Surface.*—Upper surface — smooth. Lower surface — relatively smooth with slight ridges from mid-rib and pinnate veining.

*Petiole.*—Average length 1 1/16 inches. Average width 1/16 inch. Color upper surface — pale red to pastel red (10-A-3) to (10-A-4). Color lower surface — greenish white (30-A-2).

*Glands.*—Globose. Small, alternate. Average length and width — 1/32 inch, nearly round. Number varies from 2 to 5. Average number 4. Color — dull red (10-D-5).

*Color.*—Upper surface — green to dark green (29-F-6) to (29-F-8). Lower surface — grayish green to green (29-D-5) to (29-E-5).

*Apex.*—Acuminate.

*Base.*—Obtuse.

Flower buds:

*Size.*—Medium. Average length 17/32 inch three days before bloom. Average diameter 3/8 inch.

*Hardiness.*—Hardy in all stone fruit growing areas of California.

*Form.*—Plump.

*Pubescence.*—Pubescent.

*Color.*—Pale pink to pink (11-A-3) to (11-A-4).

Flowers:

*Development.*—Complete, perigynous, single, pistil, multiple stamens, 5 petals and sepals alternately positioned.

*Size.*—Large, showy. Average height 15/32 inch. Average diameter 1 1/16 inches.

*Number of petals.*—Five, alternately arranged to sepals.

*Petals.*—Obovate, narrows at point of attachment. Average length ½ inch. Average width 7/16 inch. Color — white to pale pink (11-A-1) to (11-A-3). Color fades to white before petal fall. Surface edge varies from smooth to slightly scalloped.

*Sepals.*—Medium size. Average length 5/16 inch. Average width 3/16 inch at point of attachment. Number — Five, alternately arranged to petals. Color — upper surface — grayish orange (5-B-6). Color — lower surface — grayish red (11-C-6), fades to greenish yellow as flower ages.

*Stamens.*—Number per flower — 20 to 25. Average filament length — 39/64 inch. Filament color — white (1-A-1). Anther color — light yellow to buttercup yellow (3-A-4) to (4-A-7).

*Pollen.*—Present. Self-sterile, needs pollenizer. Color — light yellow to yellow (3-A-5) to (4-A-5).

*Pistil.*—Usually one. Average length 11/16 inch. Color — white (1-A-1). Pubescent.

*Fragrance.*—None.

*Blooming period.*—Date of First Bloom Feb. 20, 2000. Date of Last Bloom Feb. 28, 2000. Varies slightly with climatic conditions.

*Color.*—White (1-A-1).

*Pedicel.*—Average length 5/32 inch. Average width 1/8 inch. Color — wax yellow to mustard yellow (3-B-5) to (3-B-6).

Fruit:

*Maturity when described.*—Firm ripe.

*Date of first picking.*—May 1, 2000.

*Date of last picking.*—May 5, 2000. Varies slightly with climatic conditions.

*Size.*—Medium to large. Average diameter axially 1 15/16 to 2 inches. Average transversely in suture plane 2 to 2 3/8 inches. Average weight 80 grams. Average weight varies slightly with fertility of the soil, amount of thinning and climatic conditions.

*Form.*—Globose. Has a more round shape and not as compressed in suture plane as apricots.

*Suture.*—Pronounced. Extends from base to apex.

*Ventral surface.*—Lipped. Recessed approximately 1/16 inch in center between base and apex.

*Apex.*—Varies from round to slightly retuse.

*Base.*—Retuse.

*Cavity.*—Round to slightly elongated in suture plane. Average depth 1/4 inch. Average breadth 7/16 inch.

Stem:

*Size.*—Average length 1/4 inch. Average diameter 1/8 inch, enlarged at point of fruit attachment.

*Color.*—Grayish green (29-D-6).

Flesh:

*Ripens.*—Evenly.

*Texture.*—Firm, meaty.

*Fibers.*—Few, very small, tender.

*Firmness.*—Firm. Considerably firmer than standard apricot varieties.

*Aroma.*—Slight.

*Amydgalin.*—Undetected.

*Eating quality.*—Excellent.

*Flavor.*—Excellent. Predominately apricot, but suggestive of plum.

*Juice.*—Moderate, enhances flavor.

*Brix.*—Average 14.2°. Varies slightly with amount of fruit per tree and climatic conditions.

*Color.*—Light yellow to light orange (4-A-4) to (5-A-4). Flesh slightly lighter color around pit cavity. Pit cavity — grayish orange (5-B-5).

Skin:

*Thickness.*—Medium.

*Texture.*—Medium.

*Tendency to crack.*—Slight during periods of rain, varies with degree of fruit maturity.

*Color.*—Pale orange to light orange (5-A-3) to (5-A-5).

*Tenacity.*—Tenacious to flesh.

*Astringency.*—None.

Stone:

*Type.*—Freestone.

*Size.*—Medium to large. Average length 63/64 inch. Average width 55/64 inch. Average thickness 29/64 inch.

*Form.*—Ovoid.

*Base.*—Varies from straight to rounded.

*Apex.*—Acute, slight point on some stones. Length — very short — 1/32 inch.

*Surface.*—Pitted throughout. One long groove on each side of suture, usually extending from base to apex. Some stones have 2 grooves on each side of suture, the second extending approxiamtely 1/3 the distance from the base toward apex.

*Sides.*—Equal.

*Ridges.*—Small. Narrow ridges near suture extending from base approximat-*/ely 1/3 of the distance toward apex.

*Tendency to split.*—None.

*Color.*—Light brown to brownish orange (5-C-5) to (5-C-6) when stone is dry.

Use: Dessert. Market — local and long distance.

Keeping quality: Good, held firm for two weeks in cold storage without internal breakdown of flesh or appreciable loss of flavor.

Shipping quality: Good, showed minimal flesh bruising or skin scarring in packing and shipping trials in comparison to Flaming Gold Apricot (U.S. Plant Pat. No. 2,822).

Disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct interspecific tree, substantially as illustrated and described, characterized by its large size, semi-spreading growth and being a productive and regular bearer of medium to large, freestone fruit with excellent flavor that is predominately apricot, but suggestive of plum with a desirable lingering aftertaste and, in comparison to the fruit of the interspecific tree Honey Rich (U.S. Plant Pat. No. 10,292), the fruit is lighter orange in color and is 14 days earlier in maturity.

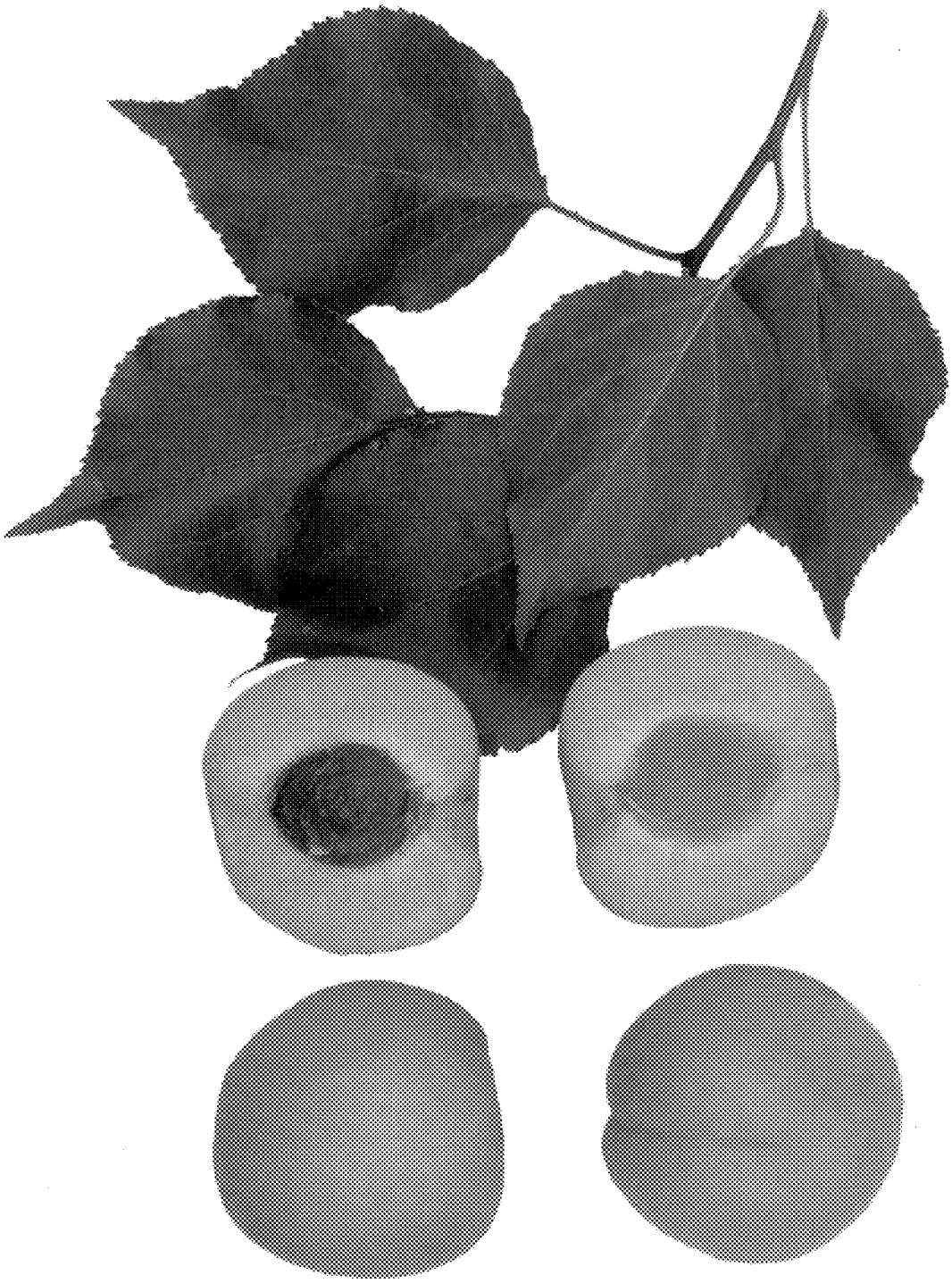

* * * * *